(12) United States Patent
Hutzler

(10) Patent No.: US 11,878,852 B2
(45) Date of Patent: Jan. 23, 2024

(54) PACKAGING AND METHOD OF MANUFACTURING THE PACKAGING FOR A PRODUCT TO BE RECEIVED THEREIN

(71) Applicant: STERIPAC GmbH, Calw (DE)

(72) Inventor: Martin Hutzler, Calw (DE)

(73) Assignee: STERIPAC GMBH, Calw (DE)

( * ) Notice: Subject to any disclaimer, the term of this patent is extended or adjusted under 35 U.S.C. 154(b) by 66 days.

(21) Appl. No.: 17/724,776

(22) Filed: Apr. 20, 2022

(65) Prior Publication Data

US 2023/0249884 A1 Aug. 10, 2023

(30) Foreign Application Priority Data

Feb. 9, 2022 (DE) .......................... 202022100736.5

(51) Int. Cl.
*B65D 75/36* (2006.01)
*B65B 5/04* (2006.01)
(Continued)

(52) U.S. Cl.
CPC .............. *B65D 75/366* (2013.01); *B65B 5/04* (2013.01); *B65B 7/28* (2013.01); *B65B 55/02* (2013.01);
(Continued)

(58) Field of Classification Search
CPC ...... B65D 75/366; B65D 75/28; B65D 75/30; B65D 75/32; B65D 75/321; B65D 75/322; B65D 75/326; B65D 81/025; B65B 7/28
(Continued)

(56) References Cited

U.S. PATENT DOCUMENTS 5,629,060 A * 5/1997 Garwood ............... B65D 25/16
156/581
5,631,036 A * 5/1997 Davis ..................... B65D 75/26
426/123

(Continued)

FOREIGN PATENT DOCUMENTS

DE 10 2013 004 168 A1 9/2014
DE 10 2018 098 288 A1 12/2016
(Continued)

*Primary Examiner* — Jacob K Ackun
(74) *Attorney, Agent, or Firm* — Birch, Stewart, Kolasch & Birch, LLP

(57) ABSTRACT

A packaging with a packaging arrangement and at least one product received therein, such as in particular a medical product, and a method for manufacturing the packaging are disclosed. The packaging arrangement has a first packaging element, which has a trough-shaped receiving space for receiving the product, wherein the receiving space is delimited by a receiving base and a peripheral wall, which is connected with the receiving base. The packaging arrangement has a second packaging element inserted into the receiving space, which element has a plastically deformable deformation region and a plug-in region which extends peripherally around the deformation region and spans the same, wherein the product is arranged between the deformation region and the receiving base and the deformation region is at least plastically deformed in sections complementarily to the product, by contacting the same. The product is elastically clamped between the receiving base and the deformation region.

13 Claims, 3 Drawing Sheets

Figure 1:
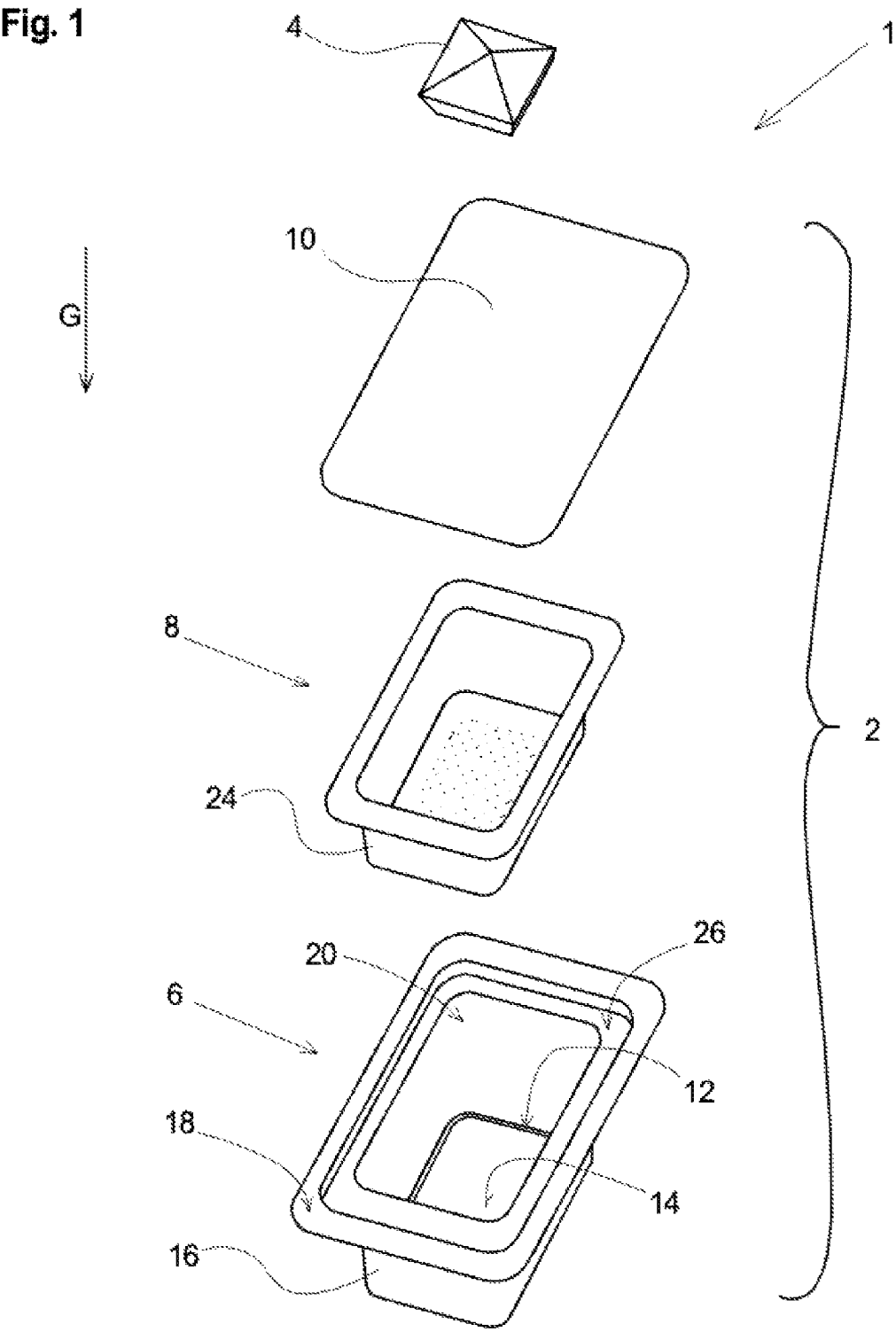

(51) Int. Cl.
  *B65B 7/28* (2006.01)
  *B65B 55/02* (2006.01)
  *B65D 75/58* (2006.01)
  *B65D 81/02* (2006.01)

(52) U.S. Cl.
  CPC ....... *B65D 75/5855* (2013.01); *B65D 81/025* (2013.01)

(58) Field of Classification Search
  USPC .................................................. 206/530, 438
  See application file for complete search history.

(56) References Cited

U.S. PATENT DOCUMENTS

| | | |
|---|---|---|
| 11,332,298 B2 | 5/2022 | Roesler et al. |
| 2012/0325714 A1* | 12/2012 | Hansen .............. B65D 73/0092 220/4.23 |
| 2014/0251845 A1 | 9/2014 | Roesler |

FOREIGN PATENT DOCUMENTS

| | | |
|---|---|---|
| DE | 10 2017 111 702 A1 | 11/2017 |
| DE | 10 2018 130 686 A1 | 6/2020 |
| EP | 3 108 842 B1 | 3/2019 |

\* cited by examiner

PACKAGING AND METHOD OF MANUFACTURING THE PACKAGING FOR A PRODUCT TO BE RECEIVED THEREIN

The invention relates to packaging with a packaging arrangement and at least one product received in the packaging arrangement, such as a medical, in particular sterilizable product, according to the preamble of claim 1. The invention also relates to a packaging arrangement and a method for manufacturing the packaging. The packaging arrangement comprises a first packaging element with a trough-shaped receiving space for receiving the product. For this purpose, the first packaging element is designed in such a way that the receiving space is delimited by a receiving base and a peripheral wall connected to the receiving base. Furthermore, the packaging arrangement comprises a second packaging element which is inserted into the receiving space and has a plastically deformable deformation region and a plug-in region which extends peripherally around the deformation region and spans the same. The product is arranged between the deformation region and the receiving base and the deformation region forms a contact region with the product by contacting the product, in which the deformation region is plastically deformed at least in sections complementarily to the surface of the product.

Such a packaging and a method for its manufacturing is known from EP 3 108 842 Bi. This document discloses a packaging arrangement with a first and second packaging element, with a deformation region of the second packaging element being heated and applied to the product. As a result, the deformation region is plastically deformed in regions that are complementary to the corresponding region of the product. As a result, a profile is formed in the contact region between the deformation region and the product, which ensures that the product is secured in position with a positive fit in relation to the packaging arrangement.

In the case of the known packaging, a certain degree of movement of the product relative to the packaging arrangement can occur in some cases with certain products, depending on their surface properties or their geometry, such as with flat, rounded and/or smooth surfaces.

The object of the invention is therefore to provide a packaging of the generic type which avoids the disadvantages mentioned and ensures stable positioning in the packaging arrangement regardless of the geometry and surface properties of the product to be packaged and which enables a cost-effective and simple manufacturing.

In the case of the packaging according to the invention, this object is achieved with the features of claim 1. It is provided that the at least one product is clamped elastically between the receiving base and the deformation region. For the purposes of the invention, elastic clamping means that the product held between the receiving base and the deformation region is subjected to an elastic restoring force or prestressing force and is thus clamped between the two elements. Due to this prestressing of the packaging arrangement acting on the product, even a small depression on the side of the deformation region is sufficient to form a stable, form-fitting engagement with the relevant complementarily designed region of the product and thereby ensure a largely play-free positioning of the product in relation to the packaging arrangement. As a result, for example, products with a largely flat or rounded geometry and/or a smooth surface are also held in a stable position relative to the packaging arrangement.

In this case, the receiving base is preferably elastically deformed and, as a result of the restoring forces generated thereby, is elastically prestressed against the product. As a result, the product can be elastically clamped into the packaging arrangement in a particularly simple manner during a packaging process, in particular by briefly applying an external force to the receiving base.

In a preferred embodiment, it is provided that the first packaging element has support means for it to stand in a stable manner on a subsurface, which support means span a support plane. In this case, the receiving base extends offset above the positioning plane with respect to the direction of gravitation. As a result, the receiving base with the positioning plane defines a cavity on the underside, the receiving base being stretched into the cavity in order to produce the elastic prestress. This offers the advantage that the receiving base can be elastically deformed and can generate a prestressing force acting against the product without impairing the stability of the first packaging element standing on the respective subsurface.

It is preferably provided that the receiving base extends at least in sections parallel to the standing surface. With a flat and horizontally aligned subsurface, it can be ensured that the product remains in its position even when the second packaging element is removed. This enables or simplifies, for example, at least partially automated manufacturing of the packaging and/or removal of the product from the packaging.

In a preferred embodiment, it can also be provided that the second packaging element is in the form of a blister. As a result, the second packaging element can be shaped in a simple manner in such a way that the deformation region projects sufficiently far into the receiving space in order to be able to produce the largest possible contact region between the deformation region and the product. In this way, a contour that is plastically deformed complementary to the surface of the product can be formed on the side of the deformation region over an extended region that is as large as possible.

In order to be able to securely fix the position of the second packaging element relative to the first packaging element, a closing element can be provided which is connected to the first packaging element with the second packaging element being interposed. In this way, in addition to the position of the second packaging element relative to the first packaging element, the product can also be permanently fixed in its elastically clamped position.

Advantageously, the closing element and the first packaging element are designed in such a way that they have mutually sealable materials, at least in the region where they contact one another. For the purposes of the application, sealable means that the closing element and the first packaging element can be connected to one another under the action of pressure and/or heat. The use of sealable materials enables simple and stable manufacturing of the airtight clamping region for the product. For this purpose, the closing element and the packaging element preferably have at least one sealable layer with components of a polyolefin, polyamide, polystyrene or polyester. In particular, the first and/or second packaging element and the closing element can be made of PET, PE, PP. As an alternative or in addition to the connection by sealing, the closing element can also be connected to the first and/or second connection element by gluing or welding.

It is advantageous that the first packaging element and the closing element have a peelable connection, as a result of which the closing element can be detached easily and quickly from the first packaging element or the packaging as a whole can be opened easily and quickly.

In addition, the above-mentioned object is achieved by a packaging arrangement for manufacturing the packaging in one of the above-mentioned embodiments.

Furthermore, to achieve the above object, the invention provides a method for manufacturing such a packaging. It is provided that in a first step the at least one product is positioned in the first packaging element with the trough-shaped receiving space, the receiving space being delimited by the receiving base and the peripheral wall connected to the receiving base. In a second step, the second packaging element is subjected to a heat treatment with the plug-in region that can be inserted in a form-fitting manner into the receiving space and spans the deformation region. The deformation region is preferably heated in such a way that it reaches a plastically deformable state. For this purpose, the deformation region is heated at least to the glass transition temperature or a deformation temperature which, depending on the thermoplastic material used, is in a temperature range from 50° C. to 170° C., preferably between 90 and 140° C. In a third step, the second packaging element is inserted into the receiving space, a clamping region for the product being formed between the deformation region and the receiving base, and the deformation region being plastically deformed at least partially by contact with the product. Furthermore, an external force is applied to the receiving base, so that it is elastically deformed and thereby generates a restoring force, which causes the receiving base to be prestressed against the product. In a fourth step, the second packaging element is then fixed to the first packaging element. By means of this method according to the invention, the packaging can be manufactured in such a way that the product contained therein is held in an elastically clamping and thus permanently fixed position relative to the packaging arrangement. Because the product is pressed into the positive fitting receptacle in the deformation region by the generated prestress, a relatively small region complementary to a section of the product and thus having a positive fit is already sufficient on the deformation region side to ensure a stable fixation of the product in all directions in relation to the packaging arrangement.

The receiving base is preferably stretched into a cavity on the underside of the first packaging element before and/or during the third step in order to produce the prestress acting on the product. This offers the advantage that the receiving base can apply a prestressing force acting against the product without impeding the stable arrangement of the first packaging element on a subsurface. In the context of the application, the cavity extends from the underside of the receiving base facing away from the product to a positioning plane, which is formed by a standing surface or support means of the first packaging element which is in contact with the subsurface.

The receiving base is advantageously heated before and/or during the third step. By supplying thermal energy, preferably above the glass transition temperature, the receiving base can be brought into a rubber-elastic state, as a result of which the deformation to be applied for prestressing can be imparted more easily or more gently with respect to the receiving base. In addition, this also allows the receiving base to be plastically deformed in regions that are complementary to its surface in the region of contact with the product.

In order to be able to apply the prestress acting on the product, provision can also be made for a negative pressure on the outside and/or an overpressure on the inside to be generated during the manufacturing of the packaging on the receiving base. The prestress acting against the product can thus be generated or maintained in a simple manner that is gentle on the receiving base with regard to its deformation.

In order to be able to fix the second packaging element or its position relative to the first packaging element, it can be provided, for example, that in the fourth step the receiving opening of the receiving space serving to receive the second packaging element is closed with the interposition of the second packaging element by means of the closing element. In addition to fixing both the position of the second packaging element and the position of the product relative to the first packaging element, this also ensures additional protection of the product against the external influences mentioned above, such as in particular dirt and/or mechanical stress.

In a further advantageous embodiment variant it can be provided that the product received in the packaging is subjected to sterilization together with the first packaging element and/or with the second packaging element and/or with the closing element. The product to be sterilized can in particular be a hip joint, a dental implant, a bone plate, a bone screw, a spinal column implant or an operating tool. Sterilization can preferably be carried out using superheated steam, hot air, ethylene oxide, plasma or gamma radiation, such as superheated steam, hot air, ethylene oxide, plasma or gamma radiation, or any other known and suitable sterilization method.

It is pointed out that all of the above-described elements and features of the various embodiments of the subject matter according to the invention can be interchanged or combined with one another, provided that an exchange or a combination thereof is not ruled out for technical reasons.

Figure 2:
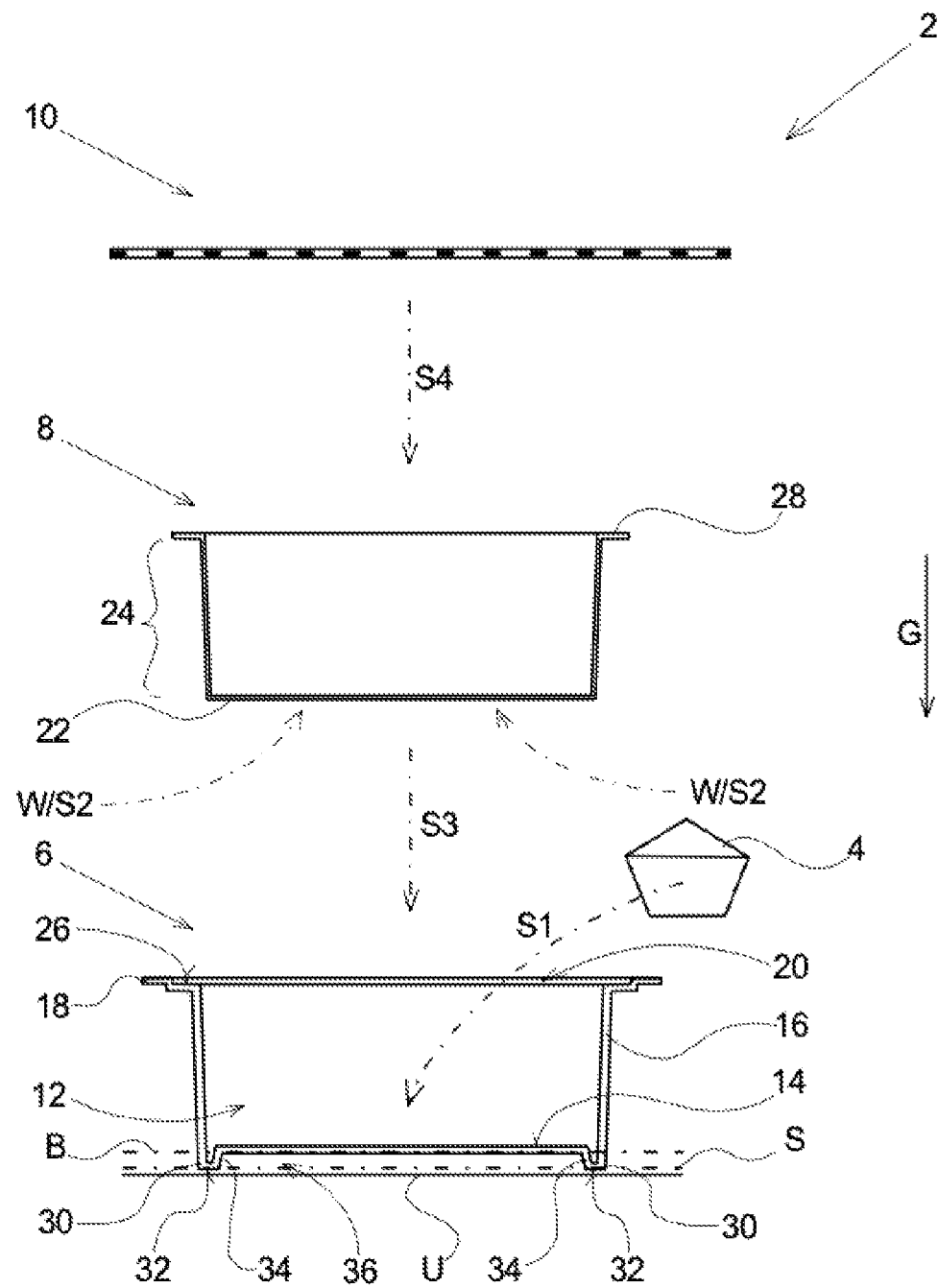
Figure 3:
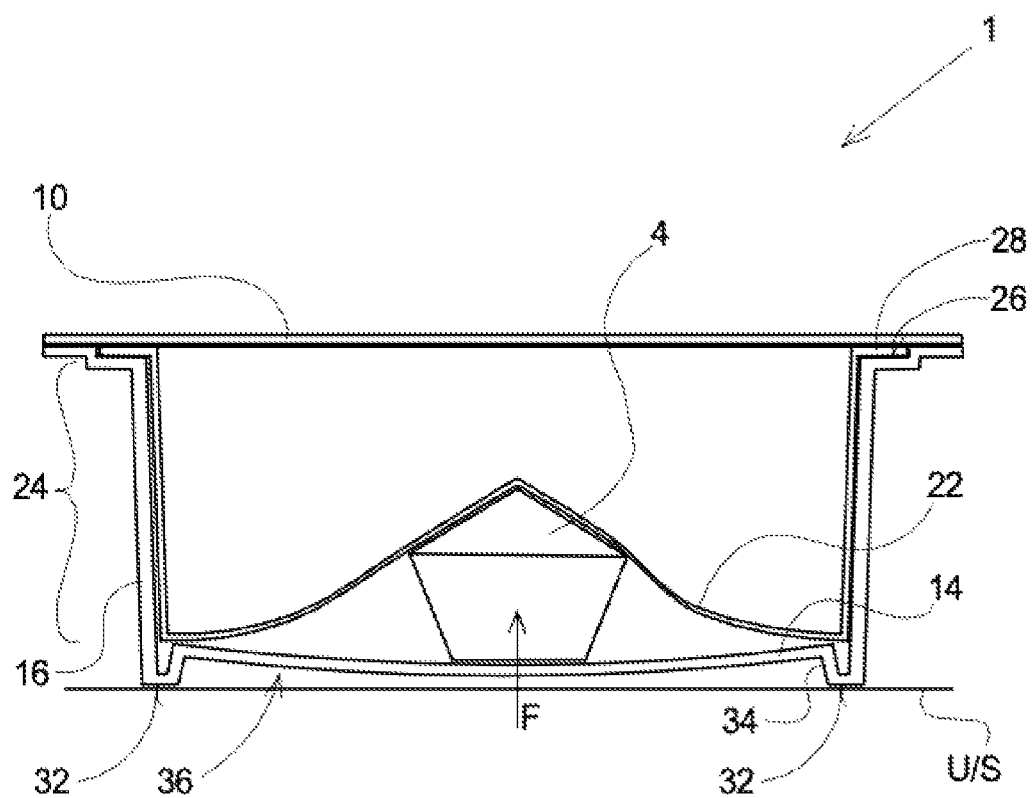

Further advantages and features of the invention result from the claims and the following description of the figures, in which exemplary embodiments of the invention are explained in detail with reference to the drawings. An exemplary embodiment of the invention is shown in the figures. In particular:

FIG. 1 shows a perspective exploded view of a packaging arrangement according to the invention, FIG. 2 shows a section through the packaging arrangement according to the invention according to FIG. 1 with the product received, FIG. 3 shows a section of a packaging made from the packaging arrangement according to FIG. 2.

FIG. 1 shows a packaging 1 with a packaging arrangement 2 for receiving a medical product 4, for example, such as in particular a hip joint, a dental implant, a bone plate, a bone screw, a spinal column implant, a surgical tool or another medical product individually manufactured, for example by laser sintering. The packaging arrangement 2 has a first packaging element 6, a second packaging element 8 and a closing element 10. The individual components of the packaging arrangement 2 are shown in the aforementioned order and counter to the direction of gravity G from bottom to top.

The first packaging element 6 is made in the form of a blister made of plastic, such as PET, PE or PP, and is essentially rigid at normal ambient temperature and forms a trough-shaped or blister-shaped receiving space 12, which is delimited by a receiving base 14 and a peripheral wall 16 connected to the receiving base 14. The wall 16 extends vertically upwards, starting from the receiving base 14, and has a collar region 18 at its end facing away from the receiving base 14. The first packaging element 6 forms a receiving opening 20 delimited by the collar region 18 via which the product 4 can be placed on the receiving base 14 in order for the product to be received within the receiving space 12. The receiving base 14 is designed to be elastically deformable.

In addition, the second packaging element 8 can also be inserted into the receiving space 12 via the receiving opening 20. This second packaging element 8 is also formed by a blister with a trough-shaped deep-drawn region, which is made of a plastic that is essentially dimensionally stable or rigid at normal ambient temperature. The second packaging element 8 forms a deep-drawn plug-in region 24 and a planar deformation region 22 that extends within the plug-in region 24 and is spanned by it. This deformation region 22 is made of a plastic that, when heated above the glass transition temperature or to a deformation temperature in the range of 50° C. to 170° C., in particular 90 to 140° C., is plastically deformable. In comparison to the deformation region 22, the plug-in region 24 is formed from a more heat-resistant plastic.

In addition, a depression 26 is embedded in the collar region 18 and is designed to complement a peripheral collar 28 of the plug-in region 24. In this way, the second packaging element 8 can be arranged in a predetermined end position within the receiving space 12 with a positive fit such that the collar 28 rests in the depression 26.

The size of the closing element 10 is adapted to the collar region 18 of the first packaging element 6 so that the second packaging element 8 inserted into the first packaging element 6 can be fixed between the first packaging element 6 and the closing element 10. Furthermore, the closing element 10 serves as a cover for closing the receiving opening 20 and thus for additional protection of the product 4.

As can be gathered in particular from FIG. 2, support means 30 are provided on the side of the wall 16 facing away from the receiving opening 20, for a stable standing support of the first packaging element 6 on the undersurface U. The support means 30 are part of the wall 16 and can be designed, for example, in the form of a peripheral base or shoulder or in the form of feet, which are divided in sections or are isolated. In the present embodiment, the support means 30 are designed in such a way that they form a standing surface 32 that spans a horizontally extending positioning plane S. Between the receiving base 14 and the standing surface 32, the support means 30 form a deformation region 34 in the manner of a film hinge, which allows additional elastic deformation in the region of the receiving base 14 and thereby the generation of additional elastic restoring forces of the same.

As can also be seen from FIG. 2, in the unloaded state, the receiving base 14 spans a base plane B, which is arranged offset in the vertical gravitational direction of the packaging arrangement 2 above the positioning plane S. In this way, a free cavity 36 is formed between the base plane B and the positioning plane S, which is delimited by the receiving base 14 and the deformation region 34.

To produce the finished, closed packaging 1 for the product 4 according to FIG. 3, in a first step the product 4 is placed in the receiving space 12, as illustrated by the arrow S1 in FIG. 2. Subsequently, in a second step S2, the deformation region 22 of the second packaging element 8 is heated by heat input W to the above-mentioned deformation temperature of, in particular, 90 to 140° C., as shown in FIG. 2.

Thereafter, in a third step, the second packaging element 8 is inserted through the receiving opening 20 into the receiving space 14 in accordance with arrow S3. The heated deformation region 22 comes into contact with the product 4, with a contour being formed on the side of the deformation region 22 which is complementary to the corresponding region of the surface of the product 4. The plastic deformation of the deformation region 22 thus forms a positive fitting receptacle for the corresponding part of the product 4.

In addition, in the third step S3, the receiving base 14 of the first packaging element 6 is stretched into the cavity 36 when the second packaging element 8 is inserted, as a result of which the receiving base 14 generates elastic restoring forces F, which prestress the product 4 in the direction of the positive fitting reception of the deformation region 22. The product 4 is clamped in a clamping region 38 formed between the receiving base 14 and the deformation region 22. The external forces required for the elastic deformation of the receiving base 14 can, for example, be applied solely via the product 4 inserted into the receiving space 12. As an alternative or in addition to this, it is also possible to apply an external force to the receiving base 14 by applying a negative pressure on the outside and/or an overpressure on the inside. In addition, the receiving base 14 can also be heated before or during the third step S3 in order to achieve improved stretching behavior.

In a subsequent fourth step, the closing element 10 is connected to the collar region 18 of the first packaging element 6 with the second packaging element 8 being interposed, as shown in FIG. 2 by the arrow S4. The attachment of the closing element 10 fixes the collar 28 of the second packaging element 8 received in the depression 26 in relation to the collar region 18 so that the position of the second packaging element 8 as a whole in relation to the first packaging element 6 is also fixed. In addition, the product 4 clamped in the clamping region 38 between the receiving base 14 and the deformation region 22 is permanently secured in its position.

In order to be able to fix the closing element 10 to the first packaging element 6, these have sealable plastic materials at least in their contact region. The connection of the closing element 10 to the collar region 18 can be made peelable, so that the packaging 1 can be opened easily and quickly, in particular by hand. As an alternative to the sealed connection, the closing element 10 can also be connected to the collar region 18 by gluing or welding, for example.

After the packaging 1 has been completed, the packaging arrangement 2 with the product 4 received therein can also be sterilized, for example by means of superheated steam, hot air, ethylene oxide, plasma or gamma radiation or by means of any other known and suitable sterilization method.

As can be seen from FIG. 3, the product 4 is fixed in position in the finished packaging 1 between the deformation region 22 and the receiving base 14. In addition to the positive fitting reception of the product 4 on the side of the deformation region 22, the product 4 is clamped in place by means of the elastic restoring force or prestressing force F acting against the product 4 or in the direction of the receiving opening 20. The result of the prestressing force F acting on the product 4 is that the product 4 is pressed into positive engagement with the complementarily shaped region of the deformation region 22 and is held stably therein. As a result, even a weakly developed contour on the side of the deformation region 22 is sufficient to be able to be held in a stable position in the clamping region 38.

It is pointed out that all of the above-described elements and features of the various embodiments of the subject matter according to the invention can be interchanged or combined with one another, provided that an exchange or a combination thereof is not ruled out for technical reasons.

The invention claimed is:

1. A packaging with a packaging arrangement and at least one product received therein, comprising:
   a first packaging element having a trough-shaped receiving space for receiving the at least one product, the receiving space being delimited by a receiving base and a peripheral wall connected to the receiving base; and
   a second packaging element inserted into the receiving space and having a plastically deformable deformation region and a plug-in region extending peripherally around the deformation region and spanning the deformation region, the at least one product being arranged between the deformation region and the receiving base,
   wherein the deformation region, due to the deformation region being in contact with the at least one product, is plastically deformed at least in regions complementary thereto, and
   wherein the at least one product is elastically clamped between the receiving base (14) and the deformation region.

2. The packaging of claim 1, wherein the receiving base is deformed and elastically prestressed against the at least one product.

3. The packaging of claim 2, wherein the first packaging element has a support spanning a positioning plane, wherein the receiving base extends with an offset in the gravitational direction above the positioning plane and thereby defines a lower-side cavity therewith, the receiving base being stretched into the cavity in order to produce the elastic prestressing.

4. The packaging of claim 3, wherein the receiving base extends at least in sections parallel to the positioning plane spanned by the support.

5. The packaging of claim 1, wherein the second packaging element is blister-shaped.

6. The packaging of claim 1, wherein a closing element for fixing the second packaging element on the first packaging element is provided, the closing element being connected with the first packaging element by interposing the second packaging element.

7. The packaging of claim 6, wherein the closing element and the first packaging element are designed in such a way that they have mutual sealable materials at least in the region where they contact one another.

8. The packaging of claim 6, wherein the first packaging element 1 and the closing element 1 have a peel able connection.

9. The packaging of claim 1, wherein the at least one product is a medical product.

10. The packaging of claim 2, wherein the second packaging element is blister-shaped.

11. The packaging of claim 3, wherein the second packaging element is blister-shaped.

12. The packaging of claim 4, wherein the second packaging element is blister-shaped.

13. The packaging of claim 2, wherein a closing element for fixing the second packaging element on the first packaging element is provided, the closing element being connected with the first packaging element by interposing the second packaging element.

* * * * *